(12) United States Patent
Hofen et al.

(10) Patent No.: US 6,596,883 B2
(45) Date of Patent: Jul. 22, 2003

(54) PROCESS FOR THE EPOXIDATION OF OLEFINS

(75) Inventors: Willi Hofen, Rodenbach (DE); Thomas Haas, Frankfurt (DE); Wolfgang Wöll, Maintal (DE); Georg Thiele, Hanau (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 10/226,766

(22) Filed: Aug. 23, 2002

(65) Prior Publication Data

US 2003/0040637 A1 Feb. 27, 2003

Related U.S. Application Data

(60) Provisional application No. 60/314,165, filed on Aug. 23, 2001.

(51) Int. Cl.$^7$ .................. C07D 301/32; C07D 301/12
(52) U.S. Cl. ................... 549/541; 549/542; 549/531
(58) Field of Search .................. 549/541, 542, 549/531

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | |
| 4,833,260 A | 5/1989 | Neri et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Rueter et al. | |
| 5,912,367 A | 6/1999 | Chang | |
| 6,042,807 A | 3/2000 | Faraj | |
| 6,063,941 A | 5/2000 | Gilbeau | |
| 6,372,924 B2 | 4/2002 | Thiele | |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 A1 | 2/2000 |
| EP | 0 100 118 A1 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0936219 | 8/1999 |
| EP | 1 066 711 | 12/1999 |
| EP | 1 122 248 A1 | 8/2001 |
| EP | 1 138 387 | 10/2001 |
| EP | 1 221 442 | 7/2002 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WO 99/11639 | 3/1999 |
| WO | WO 00/07965 | 2/2000 |
| WO | WO 00/17178 | 3/2000 |

OTHER PUBLICATIONS

European Search Report for European Application No. EP 01 12 0165, dated Jan. 30 2002, 3 pps.

*Primary Examiner*—Ba K. Trinh
(74) *Attorney, Agent, or Firm*—Smith, Gambrell & Russell, LLP

(57) ABSTRACT

A process for the working up of a product stream from the epoxidation of olefins that contains olefin, olefin oxide, water-miscible organic solvent and water, by separating this product stream into an overhead product containing olefin, olefin oxide and organic solvent, and into a bottom product containing organic solvent and water, wherein the separation takes place in a pre-evaporator with less than 10 theoretical separation stages at a pressure of 1.5 to less than 3 bar, and 20 to 60% of the total amount of organic solvent introduced with the product stream is removed with the overhead product and the balance remains in the bottom product. A process for the epoxidation of olefins that includes this working up stage is also disclosed.

32 Claims, 1 Drawing Sheet

PROCESS FOR THE EPOXIDATION OF OLEFINS

REFERENCE TO RELATED APPLICATION

The provisional application No. 60/314,165 of Aug. 23, 2001 is relied on and incorporated herein by reference.

INTRODUCTION AND BACKGROUND

The present invention relates to a process for the epoxidation of olefins, in particular to the working up of the product stream from the epoxidation reaction.

PRIOR ART

From EP-A 100 118 it is known that propene can be converted with hydrogen peroxide into propene oxide if titanium silicalite is used as catalyst. The reaction is preferably carried out in the presence of a water-miscible solvent in order to improve the solubility of propene in the reaction mixture. Preferably solvents are used that have a boiling point between the boiling points of propene oxide and water in order to be able to separate the solvent from the reaction mixture by a distillation stage and recycle it to the reaction. Methanol is preferably used as solvent.

From U.S. Pat. No. 5,599,955 it is known that the reaction mixture which is obtained in the epoxidation reaction and which consists of propene oxide, propene, possibly propane, solvent and water can be separated by a succession of distillation steps, in which the mixture is separated in a first distillation step into an overhead product containing propene oxide, propene, and possibly propane, and into a bottom product containing the solvent and water. The efficient separation of propene oxide and solvent in a distillation step requires a large number of separation stages and a high reflux ratio in the distillation column.

WO-A 99/07690 describes a process for the purification of a methanol-containing product stream from the epoxidation of propene that also contains acetaldehyde as an impurity. In this case the crude product stream from the epoxidation is subjected to a fractional distillation, in which connection it is particularly important that methanol is present in sufficient amount in the overhead product in order to achieve a substantially complete transfer of acetaldehyde to the bottom product. To this end the concentration of methanol in the overhead product is 2–6 wt. %. A distillation column with 20–60 separation stages and a reflux ratio of between 10:1 and 30:1 is furthermore necessary in order to achieve the best possible quantitative separation of the acetaldehyde. This arrangement accordingly involves high investment and operating costs for the distillation column.

From U.S. Pat. No. 5,849,938 it is known that in the distillative working up of the methanol-containing reaction mixture from the propene epoxidation, the difference in volatilities of propene oxide and methanol can be increased by carrying out the distillation as an extractive distillation using water or propylene glycol as extraction agent. The purpose of this extractive distillation is to separate methanol as well as further high boiling point impurities as quantitatively as possible from the desired product, namely propene oxide, in one distillation step. This requires a large number of separation stages and a high reflux ratio in the distillation column. In order to achieve the desired separation result, at least 10 theoretical trays, preferably 20–60 theoretical trays are required with a reflux ratio in the range from 5:1 to 15:1. The working examples disclose 25 or 50 theoretical trays and a reflux ratio of 9:1 for the extraction distillation column.

WO 00/07965 discloses a process for reacting an organic compound with a hydroperoxide especially for reacting propene with aqueous hydrogen peroxide in methanol as solvent, wherein the reaction product is subjected to a distillation step to separate a head product comprising propene, propene oxide and methanol from a bottom product comprising unreacted hydrogen peroxide. The distillation column having 15 theoretical trays is run at ambient pressure. The bottom stream is used as feed stream for a second reaction step.

In the known processes for the epoxidation of propene with $H_2O_2$ and titanium silicalite followed by distillative working up of the reaction mixture, due to the large number of separation steps and the high reflux ratio the residence time of propene oxide in the sections of the distillation column is long and there are also high concentrations of water and higher boiling point byproducts in the said sections, and accordingly the temperature is considerably higher than the boiling point of propene oxide under the distillation conditions. It has now been found that, as a result, there is an increased level of secondary reactions of propene oxide with water and other substances containing hydroxyl groups in the reaction mixture, which leads to undesirable losses of propene oxide. This disadvantage is particularly serious if the distillation is carried out under elevated pressure and thus at elevated temperature, which is advantageous for industrial exploitation since propene oxide can then be condensed with cooling water at the head of the distillation column and no expensive and energy-intensive cooling units have to be used.

This disadvantage of the known processes is exacerbated still further if the titanium silicalite catalyst used for the epoxidation reaction passes together with the reaction mixture into the separation column, since the catalyst also accelerates the undesirable secondary reactions of propene oxide with water and/or with other substances containing hydroxyl groups. If the epoxidation reaction is carried out with a suspended titanium silicalite catalyst, then in the known processes this catalyst must therefore be removed completely from the reaction mixture before the distillative separation of propene oxide and solvent. The separation of the catalyst at this point is particularly complicated since the separation is carried out in the presence of the highly volatile and carcinogenic substance propene oxide, and expensive and complicated industrial safety measures are therefore necessary. Also, precautions have to adopted in the known processes when using a fixed bed catalyst, for example by employing filtration, in order to prevent catalyst abrasion products settling in the distillation column and thereby causing product losses on account of the catalysis of the secondary reactions of propene oxide with water and/or other substances containing hydroxyl groups.

EP-A 1122248 discloses a process for the working up of a product stream from the epoxidation of olefins that contains olefin, olefin oxide, water-miscible organic solvent, hydrogen peroxide and water, by separating this product stream into an overhead product containing olefin, olefin oxide and organic solvent, and into a bottom product containing organic solvent, hydrogen peroxide and water, whereby the separation is carried out in a pre-evaporator with at most 5 theoretical separation stages at a pressure of 3 to 8 bar and 20 to 60% of the total amount of organic solvent introduced with the product stream is removed with the overhead product and the residue remains in the bottom product.

Although the process described in EP-A 1122248 results in an considerable reduction of losses of epoxidation product compared to the hitherto known processes there is still a desire in industry, and accordingly an object of this invention, to further improve the efficiency of the working up of the product stream from the epoxidation of olefins.

SUMMARY OF THE INVENTION

The above and other objects of the invention can be attained by a process for the working up of a product stream from the epoxidation of olefins that contains olefin, olefin oxide, water-miscible organic solvent, hydrogen peroxide and water by separating this product stream into an overhead product containing olefin, olefin oxide, and organic solvent, and into a bottom product containing organic solvent, hydrogen peroxide and water, wherein the separation takes place in a pre-evaporator with less than 10 theoretical separation stages and 20 to 60% of the total amount of organic solvent entrained in the product stream is removed with the overhead product, the balance remaining in the bottom product, whereby the separation in the pre-evaporator is conducted at a pressure from 1.5 to less than 3 bar, preferably 2 to 2.9 bar.

This object is furthermore achieved by a process for the catalytic epoxidation of olefins in which the olefin is reacted in a reaction step with aqueous hydrogen peroxide in a water-miscible organic solvent in the presence of a titanium silicalite catalyst, the product stream from the reaction step being optionally added to a pressure release step and then worked up according to the aforedescribed process without prior distillative separation.

It has now been found that in the epoxidation of olefins with hydrogen peroxide and a titanium silicalite catalyst using an organic water-miscible solvent, the losses of olefin oxide in the distillative working up of the reaction mixture can be further reduced compared to the process disclosed in EP-A 1122248 if the processes according to the invention are employed. Furthermore it has been surprisingly discovered that by conducting the pre-evaporation within the pressure range of the process of the present invention decomposition of unreacted hydrogen peroxide is considerably reduced. Consequently the generation of molecular oxygen by peroxide decomposition is reduced. Therefore the likelihood of generating explosive compositions in any of the subsequent work-up stages is very low so that no extra precautions have to be taken to ensure safety of the process. Thus this measure improves the overall economics of the process.

A further advantage of the present process is, that the bottom stream comprising unreacted hydrogen peroxide from the pre-evaporation can be partially recycled to the reaction step.

Still a further advantage of the present invention compared to the teaching of EP-A 1122248 is the improved energy efficiency as will be discussed in some detail below.

BRIEF DESCRIPTION OF DRAWING

The present invention will be further understood with reference to the accompanying drawing which shows a schematic flow diagram of the process of the invention.

DETAILED DESCRIPTION OF THE INVENTION

Figure 1:
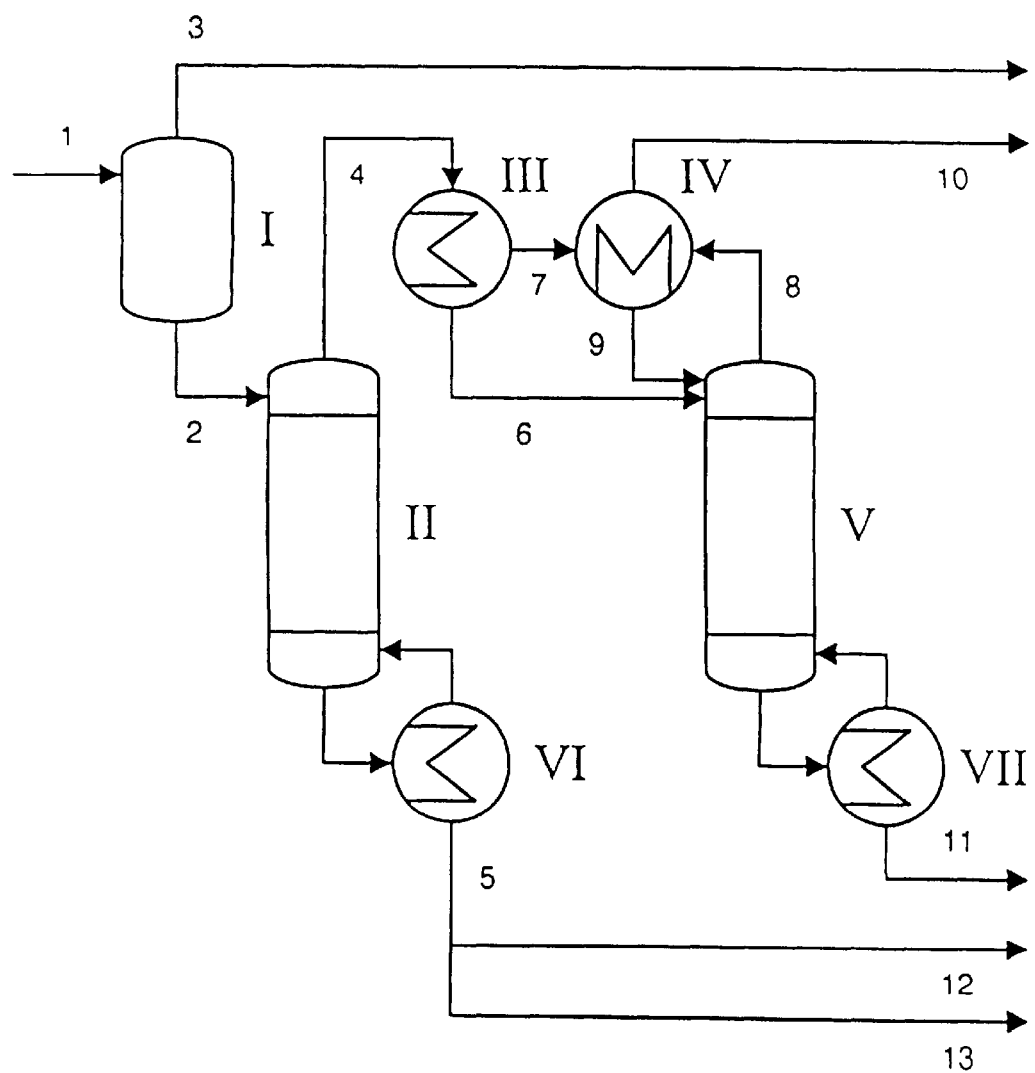

The processes according to the invention are particularly suitable for the epoxidation of olefins having two to six carbon atoms, propene being particularly preferred. The epoxidation reaction of olefins according to the invention is described hereinafter with the example of propene as preferred olefin.

The epoxidation reaction with hydrogen peroxide is carried out in the presence of a titanium silicalite catalyst in an organic water-miscible solvent. For the epoxidation of propene a solvent is preferably chosen whose boiling point is between the boiling points of propene oxide and water. Suitable solvents include, inter alia, alcohols, for example methanol, ethanol or tert.-butanol, ethers, for example tetrahydrofuran or 1,2-dimethoxyethane, and ketones, for example acetone. Methanol is preferably used as solvent.

Due to recycling of substances in the process, the solvent used may contain 0 to 20 wt. % of water. Hydrogen peroxide is used as an aqueous solution containing 10 to 90 wt. % of hydrogen peroxide. A hydrogen peroxide crude product obtained from the extraction step of the anthraquinone process and containing 30 to 45 wt. % of hydrogen peroxide is preferably used. Propene may be used mixed with propane in an amount of between 0 and 10 vol. % of propane.

In one embodiment of the invention the titanium silicalite catalyst is suspended in the reaction mixture during the reaction. The catalyst is then used in the form of a powder or in the form of a suspendable granular material that has been produced by forming in a manner known per se, for example by spray drying or fluidized bed granulation. When using a suspended catalyst, flow mixing reactors, for example stirred tank reactors or recycle reactors, as well as non-flow mixing reactors, for example tubular flow reactors, may be used for the reaction. A cascade consisting of one to three flow mixing reactors and a non-flow mixing reactor connected downstream is preferably used.

In another embodiment of the invention the titanium silicalite catalyst is used as a fixed bed over which a mixture of the feedstock materials is passed. The catalyst is then used in the form of formed bodies that have been produced in a manner known per se, for example by extrusion with the addition of binders. When using a fixed bed catalyst, reactors with bubble column characteristics are preferably used, i.e. a continuous liquid phase and a dispersed gaseous phase simultaneously flow through the reactor.

The epoxidation reaction is carried out at temperatures between 0 and 80° C., preferably between 40 and 65° C., and at elevated pressures of 10 to 40 bar, preferably 15 to 30 bar under an atmosphere substantially consisting of propene. The propene is used in excess and the residence time in the reactor is chosen so that a hydrogen peroxide conversion of more than 90%, preferably more than 95%, is achieved. The amount of solvent used is preferably chosen so as to achieve a ratio of 1 to 5 parts by weight of solvent to one part by weight of aqueous hydrogen peroxide solution.

Before the working up stage the pressure of the reaction mixture is preferably released in a pressure release stage to the pressure employed in the working up of the propene oxide. Part of the propene dissolved in the reaction mixture and possibly propane is gassed out. The resultant gas is recompressed via a compressor to the pressure prevailing in the reactor and is returned to the reaction, the propene oxide still contained in the gas preferably being removed via an absorption column together with the solvent used for the reaction, before the compression.

The reaction mixture is then separated in a pre-evaporator into an overhead product containing propene, possibly propane, propene oxide and solvent, and into a bottom product containing solvent, water, higher boiling point byproducts, such as for example propylene glycol, unreacted hydrogen peroxide and possibly suspended titanium silicalite catalyst. The pre-evaporator according to the invention has less than 10, preferably at most 5 theoretical separation steps and is preferably designed so that the stripping section corresponds to a simple evaporation and the remaining separation effect is achieved in the rectification section. The pre-evaporator is operated at a reflux ratio of at most 1.5 and if desired may also be operated totally without reflux. The pressure in the pre-evaporator is chosen in the range from 1.5 to less than 3 bar in order to avoid decomposition of hydrogen peroxide. The pre-evaporator is operated according to the invention so that between 20 and 60% of the amount of solvent fed in with the reaction mixture is removed with the overhead product and the balance remains in the bottom product. In the operational procedure according to the invention more than 95%, typically more than 98% and preferably more than 99% of the propene oxide fed in is contained in the overhead product, and more than 90%, preferably more than 97% of the water fed in is contained in the bottom product.

The product stream fed to the pre-evaporator normally contains 0.5–20 wt. % of propene, 0–4 wt. % of propane, 5–35 wt. % of propene oxide, 35–80 wt. % of methanol, 5–40 wt. % of water, 0.1–8 wt. % of higher boiling point byproducts, 0.1 to 5 wt. % hydrogen peroxide and 0–5 wt. % of titanium silicalite catalyst. This product stream is separated in the process according to the invention into an overhead product containing 1-40 wt. % of propene, 0–10 wt. % of propane, 15–75 wt. % of propene oxide, 20–85 wt. % of methanol and 0–5 wt. % of water, and into a bottom product containing 0–2 wt. % of propene oxide, 30–80 wt. % of methanol, 15–65 wt. % of water, 0.1–10 wt. % of higher boiling point byproducts, 0.1–5 wt. % of hydrogen peroxide and 0–10 wt. % of titanium silicalite catalyst.

In one embodiment the overhead product is preferably only partially condensed and the uncondensed propene, possibly mixed with propane, is recompressed via a compressor to the pressure prevailing in the reaction part and is recycled to the reaction, the propene oxide still contained in the gas preferably being removed via an absorption column together with the solvent used for the reaction, before the compression. The propene still dissolved in the condensate and possibly propane are stripped out from the condensate in a C3 stripper and the stripped-out gas is recycled to the partial condenser. The mixture of propene oxide and solvent contained in the C3 stripper is separated by distillation into a propene oxide crude product, which can be purified further in a manner known per se, and the solvent, which is recycled to the epoxidation reaction.

According to an alternative embodiment the overhead product from the pre-evaporator is partially condensed in a first condenser and the gaseous effluent from the first condenser is condensed in a second condenser maintained at a temperature below the temperature of the first condenser. Preferably the temperature within the first condenser is maintained at 40–70° C. and the temperature within the second condenser is maintained at 20–35° C. By using a two step condensation the amount of valuable propene oxide that can not be recovered is considerably reduced. Due to the low pressure in the pre-evaporation step in some instances cooling water without using a cooling unit may be insufficient in order to substantially condense the propene oxide from the overhead product. Therefore it may be advantageous to control the temperature within the first and the second condenser by using a cooling medium maintained at a temperature of 0–15° C.

A further advantage of the two step condensation is, that in case of using a cooling unit to maintain low temperatures of the cooling medium the energy consumption for cooling is reduced compared to a one step condensation.

When applying the two step condensation the condensates of both condenser are passed to a stripper to remove constituents having a boiling point that is lower than that of propene oxide, whereby the gaseous effluent from the stripper is partially condensed in the second condenser and the condensate is recycled to the stripper.

In a particularly preferred embodiment the mixture of propene oxide and solvent, preferably methanol, obtained from the C3 stripper is worked up further by extractive distillation to achieve as quantitative a separation as possible of the solvent. In this connection the mixture of propene oxide and methanol is added to the middle section of an extractive distillation column, preferably at a point corresponding to ⅓ of the total number of theoretical trays counting from the bottom, and a polar solvent with hydroxyl functionality and having a boiling point higher than that of methanol is added to the extractive distillation column at a point above the point at which the condensate enters, preferably at a point corresponding to ⅔ of the total number of theoretical trays counting from the bottom. The propene oxide crude product is distilled off at the head of the column and a mixture of methanol and the polar solvent is extracted as bottom product. The polar solvent is selected from water, glycols, glycol ethers and mixtures thereof. The preferred polar solvent is water since in this case the mixture of water and methanol can be recycled directly to the reaction step without further purification.

In order to achieve as complete a separation of the methanol as possible, a column with 25–100 theoretical separation steps and with a reflux ratio of 1–4 is already sufficient on account of the concentration of the propene oxide in the overhead product, the mathematical product of the number of separation steps and the reflux ratio typically being 75 to 125.

On account of the pre-evaporation according to the invention, according to the preferred embodiment of the process according to the invention only a very small reflux ratio for the extractive distillation step is still necessary in order to achieve the desired separation effect. Despite the two-stage procedure the operating costs for separating the water and solvent are thereby reduced compared to the prior art.

According to an especially preferred embodiment of the present invention the bottom stream comprising unreacted hydrogen peroxide from the pre-evaporation step is at least partially recycled to the epoxidation step thereby increasing the overall conversion of hydrogen peroxide. Preferably 20 to 80% of the bottom stream is recycled. Preferably the bottom stream from the pre-evaporation step is subjected to further working-up stages for example to remove water or to remove high boiling side products prior to recycling the bottom stream in order to avoid accumulation of these products in the reaction mixture.

A particular advantage of the present process is the possibility of using an energy management that results in improved energy efficiency. Due to the low pressure below 3 bar in the pre-evaporator according to the process of the present invention and in the stripper according to a preferred embodiment of the present invention as described above the pre-evaporator and/or the stripper can be heated with the condensation heat of vapors resulting from subsequent distillation steps for example from the working-up stages of the bottom stream from the pre-evaporator or the crude propene oxide stream. Thereby preferably the vapors from a subsequent distillation step are condensed in a heat exchanger whereby the condensation heat is used to evaporate a part of the bottom stream of the pre-evaporator or the stripper. The vapor is re-introduced into the bottom part of the pre-evaporator or stripper to attain the desired bottom temperature.

In case methanol is used as solvent in the epoxidation process in the working-up of the bottom stream of the pre-evaporator a distillation is conducted under pressure and methanol is separated as head product. Thereby the pressure in this distillation step is selected so that the temperature of the head product is higher than the bottom temperature of the pre-evaporator and stripper respectively. Thus the condensation heat of the head product of said distillation step can be used to heat the pre-evaporator and/or stripper in the manner as described above.

By using the above described heat management the energy efficiency of the entire process can be further improved. Consequently selection of the pressure in the pre-evaporation step according to the present invention provides the possibility to increase the over all efficiency of the process.

A particularly preferred embodiment of the present invention relates to a process for the catalytic epoxidation of propene in which a) in a reaction step the propene is reacted with aqueous hydrogen peroxide in methanol in the presence of a titanium silicalite catalyst, b) the product stream from the reaction step is optionally passed to a pressure release step, and c) the product stream is then separated, without prior distillative separation, in a pre-evaporator having less than 10 theoretical separation steps at a pressure of 1.5 to less than 3 bar into an overhead product containing propene, propene oxide and methanol, and into a bottom product containing methanol and water, 20 to 60% of the total amount of methanol introduced into the product stream being removed with the overhead product and the residue remaining in the bottom product, d) the overhead product from step c) is at least partially condensed, the condensate containing, optionally after stripping out propene and any propane present

| | |
|---|---|
| 0–12 | wt. % propene, |
| 0–5 | wt. % propane, |
| 15–75 | wt. % propene oxide, |
| 25–85 | wt. % menthol and |
| 0–8 | wt. % water, and | e) the condensate from step d) is subjected to an extractive distillation, wherein
   e1) the condensate is added to a middle section of an extractive distillation column,
   e2) a polar solvent with hydroxyl functionality and having a boiling point higher than that of methanol is added to the extractive distillation column at a point above the point at which the condensate enters,
   e3) propene oxide is distilled off at the head of the column, and
   e4) a bottom product containing methanol and the polar solvent is removed.

f) a part of the bottom product from step c) optionally after partially removing water is recycled to the reaction step a).

When using a suspended titanium silicalite catalyst the catalyst is recovered from the bottom product of the pre-evaporator by solid/liquid separation, for example by filtration or centrifugation, in which connection the solid/liquid separation can be carried out as desired either before or after the recovery of the solvent. A separation of the catalyst at this point of the process is particularly advantageous since the propene oxide, which represents a health hazard, has at this point already been separated and less stringent requirements are therefore placed on industrial safety, which considerably simplifies the overall process and makes it much more cost-effective.

The present invention will be explained in more detail with reference to FIG. 1 and a working example.

EXAMPLE

FIG. 1 illustrates the working up of the reaction mixture for a particularly preferred embodiment of the invention using a fixed bed catalyst and methanol as solvent. The reaction mixture 1 obtained from the epoxidation reaction step comprises 20.4 wt. % propene, 2 wt. % propane, 13.4 wt. % propene oxide, 0.1 wt. % low-boilers, 47.7 wt. % methanol, 15.5 wt. % water, 0.5 wt. % hydrogen peroxide and 1.1 wt. % high-boilers. The flow rate is 9.3 kg/h. The reaction mixture is directed to a pressure release unit (I) wherein the pressure is released from the reaction pressure (15–30 bar) to 2 bar.

The gas stream 3 leaving the pressure release unit (I) comprising 81 wt. % propene, 7 wt. % propane, 8 wt. % propene oxide and 4 wt. % methanol (flow rate=0.83 kg/h) is recycled to the reaction stage.

The liquid effluent 2 from the pressure release unit (I) comprising 14.3 wt.-% propene, 1.5 wt.-% propane, 13.9 wt.-% propene oxide, 51.8 wt.-% methanol, 17 wt.-% water, 0.5 wt.-% hydrogen peroxide and 1.3 wt.-% high-boilers (flow-rate=8.5 kg/h) is separated in a pre-evaporation column (II) according to the invention into an overhead stream 4 containing 34.5 wt. % propene, 3.4 wt.-% propane, 34.3 wt. % propene oxide, 25.6 wt. % methanol and 2.3 wt.-% water (flow rate 3.46 kg/h), and a bottom stream 5 containing 69.8 wt.-% methanol, 27.1 wt.-% water, 0.8 wt.-% hydrogen peroxide and 2.2 wt.-% propylene glycol monomethyl ether and other high boiling compounds (flow rate= 5.08 kg/h).

Overhead stream 4 is separated in a first condenser (III) maintained at 60° C. into a condensate 6 comprising 4.1 wt.-% propene, 0.4 wt.-% propane, 44.7 wt.-% propene oxide, 46.8 wt.-% methanol and 4.4 wt.-% water (flow rate 1.76 kg/h) and a gaseous effluent 7 comprising 66 wt.-% propene, 6.5 wt.-% propane, 23.6 wt.-% propene oxide, 3.8 wt.-% methanol and 0.1 wt.-% water (flow rate 1.7 kg/h). The condensate 6 is fed to the head of a C3-stripper (V).

The gaseous effluent 8 of the C3-stripper comprising 31.2 wt.-% propene, 3.5 wt.-% propane, 60.8 wt.-% propene oxide and 4.4 wt.-% methanol (flow rate=0.52 kg/h) and the gaseous effluent 7 from the first condenser (III) are combined and separated in a second condenser (IV) maintained at 30° C. in a gaseous effluent 10 comprising 79.5 wt.-% propene, 7.8 wt.-% propane, 11.9 wt.-% propene oxide and 0.6 wt.-% methanol (flow rate 1.5 kg/h) that is recycled to the reaction stage and a condensate 9 comprising 13.3 wt.-% propene, 1.5 wt.-% propane, 74.1 wt.-% propene oxide, 10.8 wt.-% methanol and 0.4 wt.-% water that is recycled to the C3-stripper (V).

The bottom stream 11 comprising 50.9 wt.-% propene oxide, 44.6 wt.-% methanol and 4.5 wt.-% water from the C3-stripper (V) (flow rate=1.97 kg/h) is the crude propene oxide that is subjected to further purification steps. The bottom stream 5 from the pre-evaporation column (II) can be divided in two partial streams 12 and 13, whereby stream 12 is directly recycled to the reaction stage whereas stream 13 is subjected to subsequent purification steps. Further the bottom streams 5, 11 from the pre-evaporator II and the stripper V are partially evaporated in a heat exchanger VI, VII, whereby the heat for evaporation is provided by the condensation of vapors from subsequent distillation steps in the purification of stream 13 (not shown). The evaporated part of the bottom stream 5,11 are reintroduced into the pre-evaporator II and the stripper V respectively in order to attain the desired bottom temperature.

The process according to the invention has the advantage compared to the prior art that in the working up the duration of the thermal stresses to which the olefin oxide is subjected in the presence of water and other potential reactants is substantially shorter and therefore the loss of olefin oxide by secondary reactions and the decomposition of unreacted hydrogen peroxide in the working up is significantly reduced.

The invention also has the advantage that the separation of the propene oxide from methanol and water can be achieved with smaller reflux ratios in the columns than in the prior art, which leads to savings in operating costs. With the extractive distillation that is preferably used to separate propene oxide and methanol in the crude propene oxide stream using water as extraction agent there is also the advantage, compared to the prior art, that the methanol-water mixture obtained in the bottom of the column can be returned as solvent directly to the epoxidation process, with the result that no separate distillation column is required to recover the extraction agent.

When using a suspended titanium silicalite catalyst it is possible with the process according to the invention, in contrast to the prior art, to separate the propene oxide from the reaction mixture before the recovery of the catalyst by solid/liquid separation takes place. Considerable savings in the necessary industrial safety measures are possible thanks to the solid/liquid separation in the absence of the carcinogenic propene oxide.

Finally the process of the present invention provides the possibility to use an integrated heat management in order to improve energy efficiency.

The present Invention refers to a process for the working up of a product stream from the epoxidation of olefins that contains olefin, olefin oxide, water-miscible organic solvent, hydrogen peroxide and water, by separating this product stream into an overhead product containing olefin, olefin oxide and organic solvent, and into a bottom product containing organic solvent, hydrogen peroxide and water, in a pre-evaporator with less than 10 theoretical separation stages, whereby 20 to 60% of the total amount of organic solvent introduced with the product stream is removed with the overhead product and the balance remains in the bottom product, characterized in that the separation is carried out at a pressure of 1.5 to less than 3 bar.

Preferably the reflux ratio in the pre-evaporator is at most 1.5.

It is particularly preferred that more than 95%, preferably more than 98% and particularly preferably more than 99% of the entrained olefin oxide is removed with the overhead product, and more than 90%, preferably more than 97% of the entrained water is removed with the bottom product.

The product stream from the epoxidation of olefins comprises preferably 0.1 to 5 wt-% preferably 0.3 to 3 wt-% hydrogen peroxide.

The pressure is preferably from 2 to 2.9 bar.

In a preferred embodiment of the present invention the pre-evaporator is heated with the condensation heat of vapors resulting from distillation steps of subsequent working-up stages.

According to a second aspect the present invention refers to a process for the catalytic epoxidation of olefins in which in a reaction step the olefin is reacted with aqueous hydrogen peroxide in an organic water-miscible solvent in the presence of a titanium silicalite catalyst, wherein the product stream from the reaction step is optionally fed to a pressure release step and is then worked up, without prior distillative separation, according to the process as defined above.

Thereby the olefin is preferably selected from a $C_2$–$C_6$ olefin and is preferably propene, and the solvent is selected from alcohols, ethers and ketones, and is preferably methanol.

According to a preferred embodiment of the present invention the product stream fed to the pre-evaporator contains:

| | |
|---|---|
| 0.5–20 | wt. % propene |
| 0–4 | wt. % propane |
| 5–35 | wt. % propene oxide |
| 35–80 | wt. % menthol |
| 5–40 | wt. % water |
| 0.1–5 | wt. % hydrogen peroxide |
| 0.1–8 | wt. % byproducts |
| 0–5 | wt. % titanium silicalite catalyst, | the overhead product from the pre-evaporator contains

| | |
|---|---|
| 1–40 | wt. % propene |
| 0–10 | wt. % propane |
| 15–75 | wt. % propene oxide |
| 20–85 | wt. % menthol |
| 0–5 | wt. % water | and the bottom product from the pre-evaporator contains

| | |
|---|---|
| 0–2 | wt. % propene oxide |
| 30–80 | wt. % menthol |
| 15–65 | wt. % water |
| 0.1–5 | wt. % hydrogen peroxide |
| 0.1–10 | wt. % byproducts |
| 0–10 | wt. % titanium silicalite catalyst. |

Preferably the overhead product from the pre-evaporator is at least partially condensed, constituents having a boiling point that is lower than that of olefin oxide are optionally stripped from the condensate in a stripper, and the condensate is then subjected to an extractive distillation.

More preferred the overhead product from the pre-evaporator is partially condensed in a first condenser and the gaseous effluent from the first condenser is condensed in a second condenser maintained at a temperature below the temperature of the first condenser.

Thereby the temperature of the first condenser is preferably maintained at 40–70° C. and the temperature of the second condenser is maintained at 20–35° C.

According to a preferred embodiment the condensates of both condenser are passed to a stripper to remove constituents having a boiling point that is lower than that of olefin oxide, whereby the gaseous effluent from the stripper is partially condensed in the second condenser and the condensate is recycled to the stripper.

Preferably the stripper is heated with the condensation heat of vapors resulting from distillation steps of subsequent working-up stages.

Preferably, the condensate is subjected to an extractive distillation.

According to a preferred embodiment of the present invention, the bottom stream from the pre-evaporator comprising hydrogen peroxide is at least partially recycled to the reaction step. Thereby water is preferably partially removed from the bottom stream prior to recycling to the reaction step.

Preferably, the titanium silicalite catalyst is present suspended in the reaction mixture.

The bottom product from the pre-evaporator contains titanium silicalite catalyst that is separated by solid/liquid separation.

Preferably, the titanium silicalite catalyst is present as a fixed bed.

According to a third aspect, the present invention refers to a process for the catalytic epoxidation of propene, in which a) in a reaction step the propene is reacted with aqueous hydrogen peroxide in methanol in the presence of a titanium silicalite catalyst, b) the product stream from the reaction step is optionally passed to a pressure release step, and c) the product stream is then separated, without prior distillative separation, in a pre-evaporator having less than 10 theoretical separation stages at a pressure of 1.5 to less than 3 bar into an overhead product containing propene, propene oxide and methanol, and into a bottom product containing methanol and water, 20 to 60% of the total amount of methanol introduced with the product stream being removed with the overhead product and the residue remaining in the bottom product, d) the overhead product from step c) is at least partially condensed, the condensate containing, optionally after stripping out propene and any propane present

| 0–12  | wt. % propene,      |
|-------|---------------------|
| 0–5   | wt. % propane,      |
| 15–75 | wt. % propene oxide,|
| 25–85 | wt. % menthol and   |
| 0–8   | wt. % water, and    | e) the condensate from step d) is subjected to an extractive distillation, wherein
   e1) the condensate is added to a middle section of an extractive distillation column,
   e2) a polar solvent with hydroxyl functionality and having a boiling point that is higher than that of methanol is added to the extractive distillation column at a point above the point at which the condensate enters,
   e3) propene oxide is distilled off at the head of the column,
   e4) a bottom product containing methanol and the polar solvent is removed, and f) a part of the bottom product from step c) optionally after partially removing water is recycled to the reaction step a).

Preferably the polar solvent is selected from water, glycols, glycol ethers and mixtures thereof.

What is claimed is:

1. A process for the recovery of a product stream from the epoxidation reaction of olefins that contains olefin, olefin oxide, water-miscible organic solvent, hydrogen peroxide and water, comprising separating said product stream into an overhead product containing olefin, olefin oxide and organic solvent, and into a bottom product containing organic solvent, hydrogen peroxide and water, in a pre-evaporator with less than 10 theoretical separation stages, whereby 20 to 60% of the total amount of organic solvent introduced with the product stream is removed with the overhead product and the balance remains in the bottom product, wherein the separating takes place at a pressure of 1.5 to less than 3 bar.

2. The process according to claim 1, further comprising establishing a reflux ratio in the pre-evaporator of at most 1.5.

3. The process according to claim 1, further comprising removing more than 95% of the entrained olefin oxide with the overhead product, and removing more than 90% of the entrained water with the bottom product.

4. The process according to claim 1, further comprising removing more than 95% of the entrained olefin oxide with the overhead product, and removing more than 97% of the entrained water with the bottom product.

5. The process according to claim 2, further comprising removing more than 95% of the entrained olefin oxide with the overhead product, and removing more than 90% of the entrained water with the bottom product.

6. The process according to claim 1, further comprising removing more than 98% of the entrained olefin oxide with the overhead product, and removing more than 90% of the entrained water with the bottom product.

7. The process according to claim 1, further comprising removing more than 99% of the entrained olefin oxide with the overhead product, and removing more than 90% of the entrained water with the bottom product.

8. The process according to claim 1, wherein the product stream from the epoxidation of olefins comprises 0.1 to 5 wt. % hydrogen peroxide.

9. The process according to claim 1, wherein the product stream from the epoxidation of olefins comprises 0.3 to 3 wt. % hydrogen peroxide.

10. The process according to claim 1, wherein said pressure is from 2 to 2.9 bar.

11. The process according to claim 2, wherein said pressure is from 2 to 2.9 bar.

12. The process according to claim 1, further comprising heating the pre-evaporator with condensation heat of vapors resulting from distillation of subsequent recovery stages.

13. The process according to claim 2, further comprising heating the pre-evaporator with condensation heat of vapors resulting from distillation of subsequent recovery stages.

14. A process for the catalytic epoxidation reaction of an olefin comprising reacting the olefin with aqueous hydrogen peroxide in an organic water-miscible solvent in the presence of a titanium silicalite as a reaction mixture, optionally feeding the resulting product stream from the reaction to a pressure release step and then recovering the product stream without prior distillative separation, according to claim 1.

15. The process according to claim 14, wherein the olefin is selected from a $C_2$–$C_6$ olefin, and the solvent is selected from alcohols, ethers and ketones.

16. The process according to claim 14, wherein the olefin is propene, and the solvent is selected from alcohols, ethers and ketones.

17. The process according to claim 14, wherein the olefin is selected from a $C_2$–$C_6$ olefin, and the solvent is methanol.

18. The process according to claim 14, wherein the product stream fed to the pre-evaporator contains:

| | |
|---|---|
| 0.5–20 | wt. % propene |
| 0–4 | wt. % propane |
| 5–35 | wt. % propene oxide |
| 35–80 | wt. % methanol |
| 5–40 | wt. % water |
| 0.1–5 | wt. % hydrogen peroxide |
| 0.1–8 | wt. % byproducts |
| 0–5 | wt. % titanium silicalite catalyst, | the overhead product from the pre-evaporator contains

| | |
|---|---|
| 1–40 | wt. % propene |
| 0–10 | wt. % propane |
| 15–75 | wt. % propene oxide |
| 20–85 | wt. % methanol |
| 0–5 | wt. % water | and the bottom product from the pre-evaporator contains

| | |
|---|---|
| 0–2 | wt. % propene oxide |
| 30–80 | wt. % methanol |
| 15–65 | wt. % water |
| 0.1–5 | wt. % hydrogen peroxide |
| 0.1–10 | wt. % byproducts |
| 0–10 | wt. % titanium silicalite catalyst. |

19. The process according to claim 14, further comprising at least partially condensing the overhead product from the pre-evaporator to obtain condensate, optionally stripping constituents having a boiling point that is lower than that of olefin oxide from the condensate in a stripper, and subjecting the condensate to an extractive distillation.

20. The process according to claim 14, further comprising partially condensing the overhead product from the pre-evaporator in a first condenser, obtaining a gaseous effluent from the first condenser and condensing said effluent in a second condenser maintained at a temperature below the temperature of the first condenser.

21. The process of claim 20, wherein the temperature of the first condenser is maintained at 40–70° C. and the temperature of the second condenser is maintained at 20–35° C.

22. The process of claim 20, further comprising passing the condensates of the first and second condensers to a stripper to remove constituents having a boiling point that is lower than that of olefin oxide, whereby gaseous effluent from the stripper is partially condensed in the second condenser and the condensate is recycled to the stripper.

23. The process of claim 21, further comprising passing the condensates of the first and second condensers to a stripper to remove constituents having a boiling point that is lower than that of olefin oxide, whereby gaseous effluent from the stripper is partially condensed in the second condenser and the condensate is recycled to the stripper.

24. The process of claim 19, further comprising heating the stripper with condensation heat of vapors resulting from distillation steps of subsequent recovery stages.

25. The process of claim 24, wherein the stripped condensate is subjected to an extractive distillation.

26. The process according to claim 14, further comprising at least partially recycling the bottom stream from the pre-evaporator comprising hydrogen peroxide to the reaction.

27. The process of claim 26, further comprising partially removing water from the bottom stream prior to recycling to the reaction.

28. The process of claim 14, wherein titanium silicalite catalyst is present suspended in the reaction mixture.

29. The process according to claim 28, wherein the bottom product from the pre-evaporator contains titanium silicalite catalyst that is separated by solid/liquid separation.

30. The process according to claim 14, wherein the titanium silicalite catalyst is present as a fixed bed.

31. A process for the catalytic epoxidation reaction of propene, comprising:
 a. reacting the propene in a reaction step with aqueous hydrogen peroxide in methanol in the presence of a titanium silicalite catalyst;
 b. optionally passing the product stream from the reaction step to a pressure release step; and
 c. separating the product stream, without prior distillative separation, in a pre-evaporator having less than 10 theoretical separation stages at a pressure of 1.5 to less than 3 bar into an overhead product containing propene, propene oxide and methanol, and into a bottom product containing methanol and water, removing 20 to 60% of the total amount of methanol introduced with the product stream with the overhead product and the residue remaining in the bottom product;
 d. at least partially condensing the overhead product from step c., the condensate containing, optionally after stripping out propene and any propane present

| | |
|---|---|
| 0–12 | wt. % propene, |
| 0–5 | wt. % propane, |
| 15–75 | wt. % propene oxide, |
| 25–85 | wt. % methanol and |
| 0–8 | wt. % water; and | e. subjecting the condensate from step d. to an extractive distillation, wherein
  1. the condensate is added to a middle section of an extractive distillation column,
  2. a polar solvent with hydroxyl functionality and having a boiling point that is higher than that of methanol is added to the extractive distillation column at a point above the point at which the condensate enters,
  3. propene oxide is distilled off at the head of the column,
  4. a bottom product containing methanol and the polar solvent is removed, and
 f. recycling a part of the bottom product from step c., optionally after partially removing water, to the reaction step a.

32. The process according to claim 31, wherein the polar solvent is selected from the group consisting of water, glycols, glycol ethers and mixtures thereof.

* * * * *

UNITED STATES PATENT AND TRADEMARK OFFICE
CERTIFICATE OF CORRECTION

PATENT NO. : 6,596,883 B2
DATED : July 22, 2003
INVENTOR(S) : Hofen, Willi et al.

It is certified that error appears in the above-identified patent and that said Letters Patent is hereby corrected as shown below:

Column 7,
Line 48, should read as follows: -- 25-85     wt. % methanol and --

Column 10,
Line 26, should read as follows: -- 35-80     wt. % methanol --
Line 38, should read as follows: -- 20-85     wt. % methanol --
Line 45, should read as follows: -- 30-80     wt. % methanol --

Column 11,
Line 47, should read as follows: -- 25-85     wt. % methanol and --

Column 13,
Line 8, should read as follows: -- 35-80     wt. % methanol --
Line 19, should read as follows: -- 20-85     wt. % methanol --
Line 27, should read as follows: -- 30-80     wt. % methanol --

Column 14,
Line 41, should read as follows: -- 25-85     wt. % methanol and --

Signed and Sealed this

Seventh Day of September, 2004

JON W. DUDAS
*Director of the United States Patent and Trademark Office*